United States Patent
Csikasz et al.

(10) Patent No.: US 12,121,612 B2
(45) Date of Patent: *Oct. 22, 2024

(54) POROUS SILICA MATERIAL FOR USE AS A PHARMACEUTICAL OR DIETARY ACTIVE INGREDIENT

(71) Applicant: Sigrid Therapeutics AB, Stockholm (SE)

(72) Inventors: Robert Csikasz, Stockholm (SE); Tore Bengtsson, Vaxholm (SE); Natalia Kupferschmidt, Järfalla (SE); Alfonso E. Garcia-Bennett, Stockhom (SE)

(73) Assignee: Sigrid Therapeutics AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,533

(22) Filed: Jun. 26, 2020

(65) Prior Publication Data

US 2020/0390703 A1 Dec. 17, 2020

Related U.S. Application Data

(63) Continuation of application No. 14/440,784, filed as application No. PCT/EP2013/073200 on Nov. 6, 2013, now Pat. No. 10,695,294.

(60) Provisional application No. 61/723,019, filed on Nov. 6, 2012.

(51) Int. Cl.
| | |
|---|---|
| *A61K 9/14* | (2006.01) |
| *A23L 29/00* | (2016.01) |
| *A23L 33/00* | (2016.01) |
| *A23L 33/10* | (2016.01) |
| *A23L 33/20* | (2016.01) |
| *A61K 33/00* | (2006.01) |
| *A61K 45/06* | (2006.01) |
| *C01B 33/12* | (2006.01) |

(52) U.S. Cl.
CPC .............. *A61K 9/14* (2013.01); *A23L 29/015* (2016.08); *A23L 33/10* (2016.08); *A23L 33/20* (2016.08); *A23L 33/30* (2016.08); *A61K 33/00* (2013.01); *A61K 45/06* (2013.01); *C01B 33/12* (2013.01); *A23V 2002/00* (2013.01); *C01P 2006/12* (2013.01); *C01P 2006/14* (2013.01); *C01P 2006/17* (2013.01); *Y10T 428/2982* (2015.01)

(58) Field of Classification Search
CPC .......... A61K 33/00; A61K 9/14; C01B 33/12; C01P 2006/12; C01P 2006/14; C01P 2006/17

See application file for complete search history.

(56) References Cited

U.S. PATENT DOCUMENTS

| | | | |
|---|---|---|---|
| 4,180,566 A | 12/1979 | Winyall et al. | |
| 4,185,088 A | 1/1980 | Wagner | |
| 4,824,672 A | 4/1989 | Day et al. | |
| 6,329,403 B1 | 12/2001 | Odaka et al. | |
| 6,531,100 B1 | 3/2003 | Ogata et al. | |
| 10,695,294 B2 | 6/2020 | Csikasz et al. | |
| 2004/0001862 A1 | 1/2004 | Xiu | |
| 2004/0170694 A1* | 9/2004 | Colic ................. | A61K 31/695 424/490 |
| 2009/0215774 A1 | 8/2009 | Kehler et al. | |
| 2013/0315962 A1 | 11/2013 | Garcia-Bennett et al. | |

FOREIGN PATENT DOCUMENTS

| | | |
|---|---|---|
| CN | 101296625 A | 10/2008 |
| EP | 0627627 A1 | 12/1994 |
| EP | 0778027 A2 | 6/1997 |
| EP | 1307264 A2 | 5/2003 |
| JP | 2004-345895 A | 12/2004 |
| JP | 2005-289853 A | 10/2005 |
| JP | 2010-065023 A | 3/2010 |
| KR | 20080008769 B1 | 1/2008 |
| KR | 100857411 B1 | 9/2008 |
| WO | 2002/09815 A2 | 2/2002 |
| WO | 2009/101110 A2 | 8/2009 |
| WO | 2010/050897 A1 | 5/2010 |
| WO | 2011/113879 A1 | 9/2011 |
| WO | 2012/004291 A1 | 1/2012 |
| WO | 2014/013044 A1 | 1/2014 |
| WO | 2014/078435 A1 | 5/2014 |
| WO | 2014/100522 A1 | 6/2014 |

OTHER PUBLICATIONS

Colagiuri, Ruth et al., American Journal of Public Health, Sep. 2006, vol. 96, No. 9 (Year: 2006).*
Diabetes Care, vol. 33, Supplement 1, Jan. 2010, pp. 562-569 (Year: 2010).*
Tozuka, Yuichi et al., International Journal of Pharmaceutics 386 (2010) pp. 172-177 (Year: 2010).*
Peluso, Michael R. et al., Nutrient Metabolism, Jan. 13, 1994, pp. 853-860 (Year: 1994).*
Aguilar et al., Calcium silicate and silicon dioxide/silicic acid gel added for nutritional purposes to food supplements. Scientific Opinion of the Panel on Food Additives and Nutrient Sources added to Food. The EFSA Journal. 2009;1132:1-24.
Atluri et al., Hydrothermal Phase Transformation of Bicontinuous Cubic Mesoporous Material AMS-6. Chem Mater. 2008;20:3857-3866.

(Continued)

*Primary Examiner* — Andrew S Rosenthal
*Assistant Examiner* — Lyndsey M Beckhardt
(74) *Attorney, Agent, or Firm* — McCarter & English, LLP; Steven G. Davis; Michael J. DeGrazia

(57) ABSTRACT

A porous silica material for use as a pharmaceutical or dietary active ingredient having pores in the mesoscale range (2-50 nm), wherein the average pore size of the pores in the mesoscale range is in the range of 2 to 25 nm, and the pore size distribution (PSD) in the mesoscale range is such that at least 80% of the pores fall within the range of 2 to 25 nm.

19 Claims, 8 Drawing Sheets

(56) References Cited

OTHER PUBLICATIONS

Brunauer et al., Adsorption of Gases in Multimolecular Layers. J Am Chem Soc. 1938;60(2):309-19.
Chmelka, Zeolites: Large Molecules Welcome. Nature Materials. Sep. 2006;5:681-682.
Christaki et al., Effects of Dietary Inclusion of Natural Zeolite and Flaxseed on Broiler Chicken's Body Fat Deposition in an Extended Fattening Period. Arch. Geflugelk. 2006;70(3):106-111.
EUROASPIRE II Study Group, Lifestyle and risk factor management and use of drug therapies in coronary patients from 15 countries; principal results from EUROASPIRE II Euro Heart Survey Programme. Eur Heart J. Apr. 2001;22(7):554-72.
European Centre for Ecotoxicology and Toxicology of Chemicals, Synthetic Amorphous Silica (CAS No. 7631-86-9). JACC No. 51. 237 pages, Sep. 2006.
Garber et al., Cholesterol screening in asymptomatic adults, revisited. Part 2. Ann Intern Med. Mar. 1, 1996;124(5):518-31.
Golomb et al., Statin adverse effects: a review of the literature and evidence for a mitochondrial mechanism. Am J Cardiovasc Drugs. 2008;8(6):373-418.
Hockley et al., European Cholesterol Guidelines Report. London School of Economics & Political Science (LSE), Policy Analysis Centre. 24 pages, (2007).
Jugdaohsingh et al., Dietary silicon intake and absorption. Am J Clin Nutr. May 2002;75(5):887-93.
Kaukonen et al., Enhanced in vitro permeation of furosemide loaded into thermally carbonized mesoporous silicon (TCPSi) microparticles. Eur J Pharm Biopharm. Jun. 2007;66(3):348-56.
Keller et al., Gas Adsorption Equilibria: Experimental Methods and Adsorptive Isotherms. Springer Science + Business Media, Inc., Boston. 436 pages, (2005).
Kresge et al., Ordered mesoporous molecular sieves synthesized by a liquid-crystal template mechanism. Nature. Oct. 22, 1992;359:710-2.
Kruk et al., Characterization of the Porous Structure of SBA-15. Chem Mater. 2000;12(7):1961-8.
Kupferschmidt et al., Large pore mesoporous silica induced weight loss in obese mice. Nanomedicine. doi:10.2217/NNM.13.138. 9 pages, (2013). prepublication edition.
Mahkam, Synthesis and characterization of pH-sensitive silica nanoparticles for oral-insulin delivery. Curr Drug Deliv. Nov. 2011;8(6):607-11.
Mamaeva et al., Mesoporous silica nanoparticles as drug delivery systems for targeted inhibition of Notch signaling in cancer. Mol Ther. Aug. 2011;19(8):1538-46.
Mancini et al., Diagnosis, prevention, and management of statin adverse effects and intolerance: proceedings of a Canadian Working Group Consensus Conference. Can J Cardiol. Sep.-Oct. 2011;27(5):635-62.
Mayo Clinic Staff, Statin side effects: Weigh the benefits and risks. Mayo Clinic. Retrieved online at: https://www.mayoclinic.org/diseases-conditions/high-blood-cholesterol/in-depth/statin-side-effects/art-20046013. 3 pages, May 11, 2019.
McCusker et al., IUPAC Nomenclature for Ordered Microporous and Mesoporous Materials and its Application to Non-zeolite Microporous Mineral Phases. Reviews in Mineralogy & Geochemistry. 2005;57:1-16.
Medical dictionary, anorectic. Retrieved online at: https://medical-dictionary.thefreedictionary.com/anorectic. 3 pages, (2019).
Medical dictionary, silica. Retrieved online at: https://medical-dictionary.thefreedictionary.com/silica. 4 pages, (2019).
Mukhopadhyay et al., Chemistry and biology of bile acids. Current Science. Dec. 25, 2004;87(12):1666-83.
Olivier et al., Determination of Pore Size Distribution from Density Functional Theoretic Models of Adsorption and Condensation within Porous Solids. Presented at the International Symposium on the Effects of Surface Heterogeneity in Adsorption and Catalysis on Solids; Kazimier Dolny, Poland. p. 161, Jul. 1992.
Olivier et al., Determination of Pore Size Distribution from Density Functional Theory: A Comparison of Nitrogen and Argon Results. Studies in Surface Science and Catalysis. 1994;87:81-9.
Peluso et al., A food-grade silicon dioxide is hypocholesterolemic in the diet of cholesterol-fed rats. J Nutr. Jun. 1994;124(6):853-60.
Prociuk, Weight Loss Protocol. Retrieved online at: https://web.archive.org/web/20100417140834/http://drpeterprociuk.com/weight_loss.html. 3 pages, (2009).
Reffitt et al., Silicic acid: its gastrointestinal uptake and urinary excretion in man and effects on aluminium excretion. J Inorg Biochem. Aug. 30, 1999;76(2):141-7.
Salonen et al., Mesoporous silicon microparticles for oral drug delivery: loading and release of five model drugs. J Control Release. Nov. 28, 2005;108(2-3):362-74.
Sato et al., Formation of ordered macropores and templated nanopores in silica sol-gel system incorporated with EO-PO-EO triblock copolymer. Colloids and Surfaces A: Physiochemical and Engineering Aspects. 2001;187-188:117-122.
Tonelli et al., Efficacy of statins for primary prevention in people at low cardiovascular risk: a meta-analysis. CMAJ. Nov. 8, 2011;183(16):E1189-E1202.
Wachter et al., Diatomaceous earth lowers blood cholesterol concentrations. Eur J Med Res. Apr. 8, 1998;3(4):211-5.
Ward et al., A systematic review and economic evaluation of statins for the prevention of coronary events. Health Technol Assess. Apr. 2007;11(14):1-160, iii-iv.
Xia et al., In vivo enhancement in bioavailability of atazanavir in the presence of proton pump inhibitors using mesoporous materials. ChemMedChem. Jan. 2, 2012;7(1):43-8.
Xu, Molecular Sieves and Mesporous Materials. Science Press. pp. 560-576, (2004).
International Search Report and Written Opinion for Application No. PCT/EP2013/073200, dated Mar. 3, 2014.
Kurihara, Handbook of Home-based Self-treatment and Healthcare against Cholesterol without Seeing a Doctor or Taking Medicine. Harbin Publishing, Mar. 2013.
Chinese Office Action for Application No. 201380069421.3, dated Mar. 31, 2020, 10 pages.
Bimbo et al., Drug permeation across intestinal epithelial cells using porous silicon nanoparticles. Biomaterials. Apr. 2011;32(10):2625-33.
Powell et al., Origin and fate of dietary nanoparticles and microparticles in the gastrointestinal tract. J Autoimmun. May 2010;34(3):J226-33.
Rinde et al., Mesoporous silica with precisely controlled pores reduces food efficiency and suppresses weight gain in mice. Nanomedicine (Lond). Jan. 2020;15(2):131-144.
Sakai-Kato et al., Physicochemical properties and in vitro intestinal permeability properties and intestinal cell toxicity of silica particles, performed in simulated gastrointestinal fluids. Biochim Biophys Acta. Mar. 2014;1840(3):1171-80.
Mari et al., Characterization of beta-cell function impairment in first-degree relatives of type 2 diabetic subjects: modeling analysis of 24-h triple-meal tests. Am J Physiol Endocrinol Metab. Mar. 2005;288(3):E541-6.
Oschilewski et al., dministration of silica prevents diabetes in BB-rats. Diabetes. Feb. 1985;34(2): 197-9.

* cited by examiner

Textural and structural Characterisation

Morphology...................................Sherical Cavities (SC)
Average macroporous size (SEM)............... 1.5 μm
Average mesopore size.........................12 nm
Surface area (BET).........................550 m²/g
Pore volume..................................0.9 cm³/g
(Nitrogen sorption isotherms)
Silica density......................... 2.2 g/ cm3

POROUS SILICA MATERIAL FOR USE AS A PHARMACEUTICAL OR DIETARY ACTIVE INGREDIENT

TECHNICAL FIELD

The present invention relates to a means for body fat composition (adipose tissue) lowering as well as a composition enabling this.

BACKGROUND OF THE INVENTION

Obesity and overweight is a major factor in the cause of high blood cholesterol and it is estimated that in the United States, roughly 300,000 deaths per year are directly related to obesity, and more than 80% of these deaths are in patients with a BMI over 30. For patients with a BMI over 40, life expectancy is reduced significantly (as much as 20 years for men and five years for women). Obesity also increases the risk of developing a number of chronic diseases, including: insulin resistance, type II diabetes, high blood pressure, high cholesterol, stroke, heart attacks, sleep apnea, congestive heart failure, osteoarthritis and cancer. In particular High levels of cholesterol have been associated with cardiovascular diseases as well as atherosclerosis.

There is currently only one pharmaceutical treatment for obesity: Orlistat, which is Food and Drug Administration (FDA) approved. Orlistat works by affecting the body's process of nutrient adsorption in the gastro intestinal (GI) tract, blocking fat digestion and lowering caloric absorption by inhibiting pancreatic lipases. An over the counter compound based on dietary fibers (for example, fermentable fibers based on pectin) has been additionally commercialized. Other compounds on the verge of approval are based on mechanisms of increased metabolism, or suppression of appetite. Drugs based on combination treatments have recently been suggested as suitable alternatives in improving the efficacy of pharmaceutical compounds based for weight loss. However several of those have had to be removed from the market due to the link with heart valve damage, for example fenfluramine and dexfenfluramine. Another example, Sibutramine has been withdrawn from the market in the United States, the UK, the EU, Australia, Canada, Hong Kong and Colombia. Sibutramine risks (non-life threatening myocardial infarction and stroke) outweigh the benefits of its use against obesity.

According to the World Health Organization (WHO) an 8.7% of the total burden of disease of the European Region can be addressed to high blood cholesterol. [Hockley T et al. European Cholesterol Guidelines report 2007] Furthermore, cholesterol reduction in patients with coronary disease retards or reverses the progression of atherosclerotic disease. [Garber A M et al. *Ann Intern Med,* 124:518-531, 1996] Statins are the most widely used lipid lowering drug used for prevention of coronary diseases in high risk patients although there are controversies regarding their positive effects in preventing death and cardiovascular diseases in low and moderate risk patients. [Tonelli M CMAJ 183:1189-1202, 2011; Ward S, *Health Technol Assess.* 11:1-160, 2007] There are alternatives to statins in the form of fibrates and resins, some of them are applied in combination with statin based therapies. It has been highlighted that lipid lowering treatments only have effectiveness in 51% of patients, after dietary recommendations and increased physical activity. [European Heart Journal, 22:554-572, 2001]. Furthermore, due to the large number of patients qualifying for statin based therapies, there is a large number of intolerant patients and patients with discomforts such as muscle complaints. The latter is the major symptom limiting the use of statins. [Marcini J et al. Canadian J of Cardiology, 27:635-662, 2011]. Hence, there is a need of new and more efficient lipid lowering treatment alternatives with and without the combination of lipid lowering drugs.

Silicon occurs naturally in nature as silicon dioxide (SiO2) or the corresponding silicic acids that result from the hydration of the oxide. Human serum contains 11-25 μg silicon/dL [EFSA Journal, 2009, 1132, 1-24] and remains relatively constant suggesting that it is rapidly distributed in the body and/or excreted. Absorbed silicon is mainly excreted via the urine without evidence of toxic accumulation in the body. [EFSA Journal, 2009; Reffit D M et al. *J Inorg Biochem,* 76:141-147, 1999] Hence, silicon content in the urine can be used as indicator for silicon absorption. [Reffit 1999, Jugdaohsingh R et al. *Am J Clin Nutr,* 75:887-893, 2002] Jugdaohsingh et al. showed that food-based silica is digested and absorbed from the gastrointestinal tract in humans. A mean of 40.9% of the ingested silicon was excreted within 6 h after intake with some variations depending on the silicon source, corresponding to 20 mg excreted silicon/day. [Jugdaohsingh 2002]

The intake of silica has already been proposed for lowering blood lipid or cholesterol levels e.g. in the form of: (a) fumed silica, (b) diatomaceous earth and (c) silica hydrogel:

(a) Studies performed in rats by Peluso et al. have shown that intake had a clear hypocholesterolemic effect on Cholesterol-Fed rats by reducing total levels of plasma cholesterol, with a decrease in both very-low density lipoprotein (VLDV), and low-density lipoprotein (LDL) cholesterol. [Peluso R M et al. *J Nutr Met,* 124:853-860, 1994] The intake of silicon dioxide in (a) was in the form of non-porous fumed silica (CAB-O-SIL® EH-5, typically with average size between 120 and 300 nm, and typically with BET surface area of approximately 380 $m^2/g$). No changes in body weight were observed when comparing control animals to the animals receiving silicon dioxide. [Peluso R M et al. *J Nutr Met,* 124:853-860, 1994]

(b) Wachter et al. showed a lowering effect on blood cholesterol levels in humans after oral intake of diatomaceous earth. [Wachter H et al. *Eur J Med Res,* 3:211-215, 1998; EP 0778027 A2] Diatomaceous earth is a largely amorphous silica from sedimentary rock, used as dietary food additive for improving, e.g., the shape of nails, hairs and skin (approved by the U.S. FDA as food additive). Its intake reduced blood cholesterol as well as LDL cholesterol and triglycerides. No changes of body mass were observed. [Wachter 1998]

(c) Large pore size silica hydrogel containing about 50 to 80 weight-% water can reduce lipid or cholesterol blood levels in chicken fed on high fat diet. [U.S. Pat. No. 4,180,566 A] The silica hydrogel has no effect on body weight neither under standard nor high fat diet.

The blood lipid lowering effect in the above mentioned publications was majorly adjudicated to bile acid sequestration [as also described in U.S. Pat. No. 4,185,088 A] and elimination through the stools leading to increased production of bile acids from cholesterol in the organism. Neither body fat nor body weight lowering effects are observed in the above referred publications.

Recently, ordered porous materials (e.g. silica) have been studied as carriers for the delivery of poorly water-soluble drugs and for controlled release of pharmaceutical compounds. [Salonen J, et al. *J Control Release* 108:362-374, 2005; Kaukonen A M, et al. *Eur J Pharm Biopharm* 66:348-356, 2007; Shen S. C. International Publication Number WO 2010/050897 A1, and Garcia-Bennett et al. *ChemMedChem*, 43-48, 2012].

Ordered mesoporous materials exhibit a 2-dimensional (2-d) or 3-dimensional (3-d) ordered array of cylindrical or cage type pores (in the range of 2 to 50 nm) separated by thin silica walls. Bioactive drugs can be molecularly dispersed in these pores up to a certain loading. The influx diffusion of water to the pore surfaces provides for a rapid release of poorly water-soluble drugs if the drug compound is loaded in an amorphous state.

Ordered mesoporous materials have been attracting much attention because of the regular and adjustable pore size, different pore structures, high surface area and pore volume, high concentrations of silanol groups which ease their functionalization and conjugation to other chemical entities. They are particularly useful for the selective adsorption of different molecules due to their precise pore size distribution, and as such, are readily used in sensors and for specific adsorption of gases. Numerous syntheses have been reported for mesoporous materials based on the use of templates, or porogens, for the formation of ordered porosity. The most common preparations use surfactants as the templates, allowing tailoring porosities in the orders between 1.5 and 30 nm with good control over pore size distribution, pore structure and particle size. Examples of these materials include MCM-41, AMS-6, and SBA-15. Nanoporous folic acid materials (NFM-1) have been developed by using the non-surfactant folic acid as template. [Garcia-Bennett A E, International Publication Number WO 2009/101110 A2] These materials have the 2-D hexagonal pore structure with the pore size controllable in the range between 1.8 and 3.5 nm and varied morphologies.

BRIEF SUMMARY OF THE INVENTION

It has now surprisingly been found that porous materials, in particular porous silica materials, having a certain content of porosity in the mesoscale range (2-50 nm) have an unexpected effect in terms of reduction of human or animal body fat composition.

Thus, the present invention relates to a means for body fat composition (adipose tissue) lowering as well as a composition enabling this.

In particular, the present invention relates to a weight loss and cholesterol lowering (hypocholesterolemic) active ingredient, food additive and formulation which is comprised of a porous material having a defined content of porosity in the mesoscale range. The formulation may be enhanced with the addition of other cholesterol or weight loss inducing pharmaceutical or neutraceutical compounds or administered on its own, and it is especially suited for oral administration.

According to the present invention, the mechanism of weight loss and cholesterol lowering is based on the adsorption of biomolecules (bile acids, lipids, proteins and enzymes) and water into the porous matrix of the active porous ingredient or formulation, which may be specially designed for the selective adsorption of low-density lipoprotein LDL and other gastro-intestinal molecules. This leads to a depletion of the encapsulated gastro-intestinal molecule, for example lipases and related molecules. The result of administration of the innovative active ingredient and formulation when specially designed is a decrease in body fat composition and subsequently also a decrease in weight, and a lowering of cholesterol and other blood lipids.

Whilst other porous materials have been utilized for lowering of systemic cholesterol, this invention includes materials with narrow pore size ranges that show a significantly greater specificity towards lipases and related molecules, which leads to an effective lowering of body fat composition which in turn can result in a weight decrease effect with lower or no secondary effects compared to other existing weight decrease treatment alternatives.

In particular, the present invention relates to an oral dietary and/or pharmaceutical formulation comprising at least a porous silica material, which when administered orally as e.g. a pill, powder, suspension, as a gel or in solution results in body fat composition (adipose tissue) lowering over time, with or without subsequent weight reduction.

The invention relates also to the preparation of an oral dietary and/or pharmaceutical formulation comprising at least a porous amorphous silica material, which when administered as a pill, powder, suspension, as a gel or in solution results in overtime weight reduction. The lowering of body fat composition may be accompanied with a lowering of blood cholesterol levels and other biomolecules.

Whilst NFM-1 materials [Garcia-Bennett A E, WO 2009/101110 A2] are useful for the present invention, a higher degree of body weight loss and cholesterol adsorption is found in materials with pore sizes in the orders between 3 and 100 nm. Thus, further improvements can additionally be obtained by incorporating hierarchical porous structures; defined here by having pores in several orders of magnitude, for example macropores (50 nm and above) in addition to mesopores (2 to 50 nm), within one porous matrix. Examples of such hierarchical materials with silica and alumina compositions are well characterized by the work of Nakanishi et al. [Colloids and Surfaces A: Physicochemical and Engineering Aspects 187-1188:117-122, 2001]

Even if porous silica materials are preferred, the present invention does not exclude the use of other porous material compositions, for example amorphous alumina compositions, or porous silicon compositions, or amorphous porous carbon compositions, where the selective adsorption of similar biomolecules may be also achieved.

It is worth noting that the present invention does not relate to the use of, e.g., diatomaceous earths (a naturally occurring compound), but to a synthetic porous material, preferably silica, with sharp pore size distributions in the meso-scale (i.e. between 2 and 50 nm). The present invention discloses that the use of lower pore sizes have a specific scavenging effect for cholesterol molecules, unlike the unspecific binding observed with large pore diatomaceous earths.

Thus, in its more general definition, the present invention relates to a porous silica material for use as a pharmaceutical or dietary active ingredient having pores in the mesoscale range (2-50 nm), wherein the average pore size of the pores in the mesoscale range is in the range of 2 to 25 nm, and the pore size distribution (PSD) in the mesoscale range is such that at least 80% of the pores fall within the range of 2 to 25 nm.

Advantageously, the average pore size of the pores in the mesoscale range is in the range of 7 to 15 nm, preferably 8 to 13 nm, more preferably 10 to 12 nm.

Advantageously, at least 90%, more preferably at least 95% of the pores in the mesoscale range fall within the defined range of 2 to 25 nm.

Preferably the BET surface area is between 300 and 1300 m2/g.

Advantageously, the BET surface area is between 450 and 950 m2/g, preferably between 500 and 900 m2/g, more preferably between 550 and 850 m2/g, more preferably 600 and 800 m2/g.

Preferably the pore volume measured by nitrogen adsorption is in the range of 0.3 to 1.7 cm3/g, preferably 0.7 to 1.6 cm3/g, more preferably 0.8 to 1.5 cm3/g, more preferably 0.9 to 1.4 cm3/g.

In an embodiment of the porous silica material according to the present invention, the porous silica material additionally has a hierarchical porous structure containing both pores in the mesoscale range and macropores, where macropores are defined as pores larger than 50 nm. Thus, in addition to the mesopores, the porous materials of the invention may include macropores (i.e. pores above 50 nm). In particular, the porous materials of the invention may contain a hierarchical porous structure as defined by pores in the range between 2 nm and 50 nm and macropores in the size between 50 nm and 5 um.

The porous silica material of the invention is suitable for use in lowering of animal or human body fat composition.

Other possible uses of the porous silica material of the invention is in the prophylaxis or treatment of: obesity or metabolic syndrome (as defined by the International Diabetes Federation) or dyslipidemia or elevated blood pressure or hypertension or type 2 diabetes or insulin resistance or hyperglycemia.

Other possible uses of the porous silica material of the invention is for lowering triglyceride or cholesterol including lowering ApoB or lowering non-HDL cholesterol or lowering LDL-c or raise HDL-c levels in the blood.

A further use of the porous silica material of the invention is for lowering glucose levels in the blood.

A pharmaceutical composition comprising a porous silica material as described in the present application as an active ingredient is also part of the present invention.

The pharmaceutical composition according to the invention may advantageously contain a further active pharmaceutical ingredient or combination of ingredients.

The pharmaceutical composition according to the invention can be in the form of a pill, a powder or a suspension for oral administration.

As an example, said further active pharmaceutical ingredient or combination of ingredients can be an ingredient or combination of ingredients with weight lowering properties.

In another embodiment of the invention the formulation may be an active pharmaceutical or dietary ingredient comprising solely of a porous silica material, in which the silica composition does not exceed a chloride concentration of 250 ppm, or a heavy metal concentration of 25 ppm.

A food composition comprising a porous silica material as described in the present application as an active ingredient is also part of the present invention.

The food composition according to the invention may advantageously comprise a liquid or solid flavorant.

In general, a porous material for use as a pharmaceutical or dietary active ingredient having pores in the mesoscale range (2-50 nm), wherein the average pore size of the pores in the mesoscale range is in the range of 2 to 25 nm, and the pore size distribution (PSD) in the mesoscale range is such that at least 80% of the pores fall within the range of 2 to 25 nm, is part of the present invention.

DETAILED DESCRIPTION OF THE INVENTION

Main Component of the Active Ingredient: Mesoporous Silica Material.

Mesoporous silica materials, which were invented in 1992 (Kresge et al. *Nature* 359:710-712, 1992), are synthetic materials with pores in the mesoscale range (between 2 to 50 nm) and amorphous pore walls. They have large surface areas in the range of about 300 to 1500 m2/g (as measured by nitrogen adsorption).

The present invention relates to the use of porous materials, in particular porous silica materials, for lowering of animal or human body fat composition wherein the porous silica has narrow pore size distributions in the mesoscale range, the average pore size being about 2 to 25 nm (as measured by nitrogen adsorption and calculated using the Density Functional Theory) and BET (Brunauer-Emmett-Teller theory) surface areas between 300 and 1300 $m^2/g$. Preferred ranges of surface area values are between 450 and 950 $m^2/g$, or 500 and 900 $m^2/g$, or 550 and 850 $m^2/g$, or 600 and 800 $m^2/g$ In one embodiment the porous silica has a narrow pore size distribution in the mesoscale range of about 2 to 25 nm as measured by nitrogen adsorption and calculated using the Density Functional Theory.

Preferably, the porous silica has a narrow pore size distribution in the mesoscale range of about 7 to 15 nm as measured by nitrogen adsorption and calculated using the Density Functional Theory. More preferably, the porous silica has a narrow pore size distribution in the mesoscale range of about 8 to 13 nm as measured by nitrogen adsorption and calculated using the Density Functional Theory.

Even more preferably, the porous silica has a narrow pore size distribution in the mesoscale range of about 10 to 12 nm as measured by nitrogen adsorption and calculated using the Density Functional Theory.

For the purposes of the present invention, with the term narrow pore size distribution in the mesoscale range it is meant that at least 80% of the mesopores (i.e. of the pores in the range 2-50 nm) fall within the above-defined pore range.

Preferably at least 85% of the mesopores fall within the above-defined pore range; more preferably at least 90% of the mesopores fall within the above-defined pore range; even more preferably at least 95% of the mesopores fall within the above-defined pore range.

The present invention differs from the publications and patents referred to in the background, by the sharp pore size distributions in the mesoscale range which allows for higher adsorptive selectivity and a water content below 15% prior to preparation of the final formulation. The present invention does not include any washing with ammonium hydroxide solution at any step of its preparation.

Mesoporous amorphous silica is here defined as a material not possessing long range order in the atomic scale and capable of adsorbing a certain amount of nitrogen gas above a level of 50 $cm^3/g$ (as measured by nitrogen adsorption experiments). Amorphous silica materials adsorbing nitrogen below the aforementioned level and for the purpose of this invention are considered to be non-porous and are hence excluded from the present invention. Porous silica materials useful for the present invention may otherwise be referred to as colloidal silica but may also be known as: precipitated silicon dioxide, silica gel, hydrous silica, hydrated silicic acid, polysilicic acid gel and E551; generally described under CAS Nos.: 7631-86-9 (Silica), 112945-52-5 (Silica, amorphous, fumed, crystalline-free) and 112926-00-8 (Silica gel and precipitated silica, crystalline-free). The present invention excludes the use of diatomaceous earths and zeolites, since the former show little specificity in the context of the present invention, and the latter is not amorphous silica but a porous crystalline material. In order for silica to be useful in the present invention a pore size larger than 2 nm is necessary. An example of a porous silica composition that may be used in the present invention as an active ingredient or as part of a formulation is included in Table 1. The method of characterization is also included as defined by the Pharmacopeia.

TABLE 1

| Test parameter | Specification | Method | Result |
| --- | --- | --- | --- |
| Characters, appearance | White or almost white, light, fine, amorphous powder | Ph Eur 7.3 January 2011: 0434 | White, fine powder |
| Identification | To pass test | Ph Eur 7.3 January 2011: 0434 | Passed test |
| pH | 3.5-5.5 | Ph Eur 7.3 January 2011: 0434 | 4.24 |
| Chlorides | Max 250 ppm | Ph Eur 7.3 January 2011: 0434 | <250 ppm |
| Heavy metals | Max 25 ppm | Ph Eur 7.3 January 2011: 0434 | <25 ppm |
| Loss on ignition | Max 5% | Ph Eur 7.3 January 2011: 0434 | 2.25% |
| Assay | 99.0-100.5% | Ph Eur 7.3 January 2011: 0434 | 100.0% |

A minimum particles size distribution of 300 nm (as measured by Scanning Electron Microscopy) is required for the best mode of use with respect to silica compositions used for the present invention. Particles below this size may lead to systemic adsorption of silica and cause increased silicon levels in blood. Particles above this size are not associated with systemic adsorption and are rapidly cleared from the GI tract through feces. The present invention does not identify a particular particle shape or size, and several shapes with a variety of aspect ratios from fibers to spheres are described in the examples.

Composition of the Formulation

The present invention refers to a formulation that may comprise the active ingredient (silica) in several different compositions, namely (note that all concentrations below refer to weight percentages):

In one embodiment of the present invention the formulation contains between 95% and 100% of porous amorphous silica (main component of the present invention) acting as a pharmaceutical active ingredient or dietary ingredient;

In another embodiment of the present invention the formulation contains between 1% and 99% of a pharmaceutical active ingredient or dietary ingredient composed of porous amorphous silica (main component of the present invention), and between 1 to 99% of a secondary pharmaceutical active ingredient. Examples of secondary pharmaceutical active ingredients and combinations of these include those included in the following formulations, or groups of compounds; Orlistat (Xenical), Lorcaserin, Sibutramine (Reductil or Meridia), Rimonabant, Metformin, Exenatide, Exenatide, Pramlintide (Symlin) a synthetic analogue of the hormone Amylin, phenylpropanolamine and other amphetamines.

In another embodiment of the present invention the formulation contains between 5% and 99% of a pharmaceutical active ingredient or dietary ingredient composed of porous amorphous silica (main component of the present invention), and a secondary active ingredient such as fat-soluble vitamins (A, D, E and K), pro-vitamins, and commercially available stabilized forms of fat-soluble vitamins, and water soluble vitamins in concentrations between 1% and 95%.

In another embodiment of the present invention the formulation may contain excipients. Excipients are components of a finished drug product other than the active pharmaceutical ingredient and are added during formulation for a specific purpose. Although listed as inactive ingredients by FDA, excipients generally have well-defined functions in a drug product.

In another embodiment of the present invention the formulation may contain excipients such as: cellulose derivatives such as Methyl cellulose, Ethyl cellulose, Hydroxyethyl cellulose, Hydroxypropyl cellulose, Hydroxyethyl methylcellulose, Hydroxypropyl methyl cellulose, Carboxymethyl cellulose etc; vinyl polymers such as Polyvinyl alcohol, polyvinylpyrrolodone, poly (vinylpyrrolidone-co-vinyl acetate) etc.; and ethylene polymers like PEG. The invention may in addition contain as further constituents conventional pharmaceutical auxiliary substances such as suitable filler, binder, disintegrants, lubricants, glidants, swellable erodible hydrophilic materials, insoluble edible materials, taste-masking and odor-masking, salts, sugars, sweeteners, plant extracts, surfactants. Examples of surfactants include TPGS, Tween® 20, Crenophor® RH40 etc. Similar to surfactants, cyclodextrins are well known for their stabilizing capability and capacity.

In another embodiment, the present invention may be used together with other pharmaceutical active compounds.

The porous materials of the present invention, when used together with secondary active pharmaceutical compounds, can allow for lower effective doses of the second active component.

This can allow for lower secondary effects of the second active component and hence also better patient compliance with respect to the second active component in the formulation.

The present invention can be evaluated when administered in combination with statins, orlistat or other active pharmaceutical ingredients typically used by the target population, using obesity models such as C57BL/6J mice with diet induced obesity and hypertension.

Incorporation Methods of Pharmaceutical and Dietary Active Agents

In a certain embodiment of this application the active ingredient is used together with a separate active pharmaceutical ingredient capable of lowering cholesterol. In the case of co-administration the present invention is best administered as pill, tableted together with the additional ingredient. Tableting technologies such as the formation of pills, capsules, solutions, dispersions, emulsions, or others may be utilized. The use of these has no effect neither in the cholesterol lowering properties, nor in the weight loss properties obtained so long as the administration is given orally.

In another embodiment of the invention the formulation may be used together with pharmaceutical active compounds which are employed to reduce blood cholesterol, and have a boosting effect to their action.

In another embodiment of the invention the formulation may be used together with naturally derived active compounds, including plant, fruit, or vegetable extracts, concentrates, fibers, roughage, which are employed to reduce blood cholesterol, and have a boosting effect to their action.

In another embodiment of the invention the formulation may be used together with other porous materials including clays, husks, nutshells, seashells, $CaCO_3$, and other naturally occurring porous materials which have the ability to uptake water, fats, lipids and cholesterol.

Mechanism of Action

Mesoporous silica's large surface area may act similar to dietary fibers and adsorb lipids or bile acids within the gastrointestinal tract, hence reducing their absorption and re-sorption, respectively. Silica may adsorb fatty acids, lipids, water, enzymes, proteins and bile acids leading to their subsequent excretion and affecting the gastrointestinal concentration of the aforementioned. In turn this may lead to an increase of hepatic bile acid biosynthesis which results in a further lowering effect on blood cholesterol levels. Examples of lipids are mono-, di-, or tri-acylglycerols and related molecules. Examples of bile acids include; cholic acid, chenodeoxycholic acid, deoxycholic acid and related molecules biosynthesised from cholesterol [for further examples see Maitra et al CURRENT SCIENCE, VOL. 87, NO. 12, 25 Dec. 2004] Examples of enzymes that may be adsorbed or inhibited include gastric lipases, pancreatic carboxyl ester hydrolaze and pancreatic lipase-related protein 2 which are major players in lipid and fat digestion. The intake of mesoporous silica may also result in alterations in the end-products of bile acid bacterial metabolism, modulating either the synthesis of cholesterol or its catabolism to bile acids. The present invention excludes active ingredients that result in systemic adsorption or increases in silicon blood levels after oral administrations.

The present invention leads to a lowering of body fat composition and body weight after oral administration, which makes it different from the publications and patents mentioned in the Background of the invention as (a), (b) and (c), where administration of silica leads to a lowering of blood lipids (cholesterol) but not to any changes in body weight or composition. Also different from previous publications and patents, no changes in blood levels of cholesterol, HDL or triglycerides are observed after oral administration of the present invention for 12 weeks (see Example 4).

TABLES AND FIGURES

The present invention is not limited to the tables and figures listed below, but these are included in order to exemplify the present invention.

Table 1. Example of a porous silica composition that may be used in the present invention as an active ingredient or as part of a formulation. The method of characterization is also included as defined by the Pharmacopeia.

Table 2. Examples of textural properties of porous silica materials that may be suitable for the present invention.

FIGS. 1, 2 and 3, Example 2A. The example is included to show the effect of a typical Silica 2 material (Table 2) on lowering of body fat composition and body weight.

FIG. 1. Scanning electron microscopy image (FIG. 1A) and pore size distribution (FIG. 1B) of a mesoporous silica material included in the present invention.

FIG. 2. Development of female mice body weight, body fat composition and lean during the study described in Example 2A. The figure shows a significant effect of the silica particles with an average pore size of about 11 nm (FIG. 1) on lowering body fat composition and body weight.

FIG. 3. Development of male mice body weight, body fat composition and lean during the study described in Example 2A. The figure shows a significant effect of the silica particles with an average pore size of about 11 nm (FIG. 1) on lowering body fat composition and body weight.

FIGS. 4, 5 and 6, Example 2B. The example is included to show that a material with structural properties typical for a Silica 1 (Table 2) material has a weaker effect than a typical Silica 2 (Table 2) material on lowering body fat composition and body weight.

FIG. 4. Scanning electron microscopy image (FIG. 4A) and pore size distribution (FIG. 4B) of a mesoporous silica material included in the present invention.

FIG. 5. Development of female mice body weight, body fat composition and lean during the 20 weeks study described in Example 2B. The figure shows the effect of the silica particles with an average pore size of about 3 nm (FIG. 4) on lowering body fat composition and body weight.

FIG. 6. Development of male mice body weight, body fat composition and lean during the study described in Example 2B. The figure shows the effect of the silica particles with an average pore size of about 3 nm (FIG. 4) on lowering body fat composition and body weight.

FIGS. 7 and 8, Example 2C. The example is included to show that a material with structural properties typical for a Silica 5-type (Table 2) material has a weaker effect than a typical Silica 2 (Table 2) material on lowering body fat composition and body weight.

FIG. 7. Scanning electron microscopy image (FIG. 7A) and pore size distribution (FIG. 7B) of a mesoporous silica material included in the present invention.

FIG. 8. Development of male mice body weight, body fat composition and lean during the study described in Example 2B. The figure shows the effect of the silica particles with an average pore size of about 3 nm (FIG. 4) on lowering body fat composition and body weight.

FIG. 9. Food intake and silica concentration in blood (measured by inductively coupled plasma technique) of mice included in Example 2A and 2B.

FIG. 10. Lipid (Cholesterol, HDL and tryglicerides) and glucose levels in blood from female mice receiving Particle 2 material (representative of Silica 2 as described in Table 2) in the diet, compared to control mice not receiving mesoporous silica in the diet.

FIG. 11. Lipid (Cholesterol, HDL and tryglicerides) and glucose levels in blood from female mice receiving Particle 1 material (representative of Silica 1 as described in Table 2) in the diet, compared to control mice not receiving mesoporous silica in the diet.

FIG. 12. Lipid (Cholesterol, HDL and tryglicerides) levels in blood from male mice receiving Particle 1, Particle 2 and Particle 3 in the diet (representative of respectively Silica 1, 2 and 3 as described in Table 2), compared to control mice not receiving mesoporous silica in the diet.

FIG. 13. Example of a Bimodal Pore Mesoporous material with macropores (which is representative for Silica 5 described in Table 2).

EXAMPLES

Example 1: Examples of Textural Properties of Porous Silica Materials that May be Suitable for the Present Invention The textural properties of materials that may be suitable for the present invention were determined and are included in Table 2.

The pore structure.

The pore structure was determined based on diffraction patterns recorded utilizing low-angle X-ray powder diffraction using CuKa radiation ($\lambda=1.5418$ Å at 45 kV and 40 mA) and/or transmission electron microscopy (TEM) with a TEM microscope operating at 300 kV (Cs 0.6 mm, resolution 1.7).

BET (Brunauer-Emmett-Teller) Surface Area

The BET surface area, pore volume and pore size distribution (PSD) is determined by nitrogen adsorption technique. Nitrogen adsorption/desorption isotherms were measured at liquid nitrogen temperature ($-196°$ C.) using a Micromeritics ASAP2020 volumetric adsorption analyzer for mesoporosity determination. The material samples were outgassed before the measurement. The BET equation was used to calculate the surface area from adsorption data obtained in the relative pressure ($p/p°$) range of 0.05 and 0.3. The pore volume was calculated from the amount of gas adsorbed at $p/p°=0.91$. The mesopores pore size distribution curves were derived using the density functional theory (DFT) assuming a cylindrical pore model; the pore size and PSD range of the mesopores were obtained from those curves according to the methodology described in "Gas Adsorption Equilibria: Experimental Methods and Adsorptive Isotherms by Jürgen U. Keller, Springer, 2006".

The macropores size (defined as pores larger than 50 nm) was determined using mercury porosimetry technique and/or by scanning electron microscopy (SEM) by measuring the pore width on SEM images recorded with an SEM microscope with no gold coating Example 2A: A Large Pore Mesoporous Silica Material (Particle 2 which is Representative for Silica 2 Described in Table 2)

Example of the effect of oral administration of mesoporous silica particles of about 10 nm pore size (Particle 2) on body weight, body fat composition and lean mass as compared to No silica particles (Control) in obese mice.

FIG. 1A shows a scanning electron microscopy (SEM) image of the material (named Particle 2) utilized in the study, which is representative for Silica 2 described in Table 2. The material's pore size distribution measured by nitrogen adsorption experiments is shown in FIG. 1B indicating a sharp pore size distribution in the range of about 8 to 12 nm.

Particle 2 material is utilized to exemplify the effect of mesoporous silicas on body weight and body fat composition (adipose tissue) when administered orally in a well-known obesity murine model.

From week 0 to 7.5 the animals were high fat fed in order to make them obese; from week 7.5 to 12 silica particles (Particle 2) were added into the high fat diet; from week 12 to 20 the animals received standard diet ad libitum with two extra high fat meals per week containing silica particles.

FIGS. 2 A, C and E show the development of body weight, body fat composition and lean respectively during the 20-week long study for female animals.

FIGS. 2 B, D and F shows only the data from the last eight weeks of the experiment. The stars indicate statistically significant differences between mice receiving particles in the diet compared to control mice not receiving particles in the diet.

FIG. 3 shows the same as FIG. 2 for a study with the same experimental set-up, but performed on males.

Both body fat composition and body weight decrease is observed in the animal groups receiving mesoporous silica in the diet, as compared to the control group not receiving porous silica, in both female and male mice (FIGS. 2 and 3 respectively).

A mesoporous material with pore sizes in the order above 10 nm, was utilized to exemplify the positive weight and cholesterol lowering properties of a porous silica. The effect of silica mesoporous particles with large pores, above 10 nm intake on blood lipid levels in obese black 6 mice (C57BL/6J) with elevated lipid/cholesterol blood levels and healthy animals is analyzed. Particles are embedded in the food pellets and given to the animals during a period of time of about 12 weeks. Blood levels of cholesterol, high-density lipoprotein cholesterol, low-density lipoprotein cholesterol

TABLE 2

|  | Silica 1 | Silica 2 | Silica 3 | Silica 4 | Silica 5 |
| --- | --- | --- | --- | --- | --- |
| Pore structure | 2-d-cylindrical hexagonal | 2-d-cylindrical hexagonal | hierarchical | hierarchical | Worm-like |
| BET surface area (m$^2$/g) | 653 | 709 | 300 | 550 | 685 |
| Pore size by DFT | 2 nm | 11 nm | 12 nm mesopores, and 2 µm*\ macropores | 12 nm mesopores, and 1.5 µm macropores | 30 nm |
| Pore volume (cm$^3$/g) | 0.32 | 1.17 | 1 | 0.9 | 1.6 |
| PSD range | 2-3.5 nm | 8-13 nm | 10-15 nm and, 1-3 µm | 10-15 nm and, 1-3 µm | 5-33 nm | and triglycerides are analyzed during the 12 weeks of particle intake. Levels of silica in blood are measured at the end of the experiment.

Example 2B: A Small Pore Mesoporous Silica Material (Particle 1 which is Representative for Silica 1 Described in Table 2)

Another study was performed as described in Example 2A, but utilizing a mesoporous silica material with a pore width of about 3 nm (Particle 1) instead of the material named Particle 2. FIG. 4A shows the SEM image of Particle 1 which is representative for Silica 1 described in Table 2. The material's pore size distribution measured by nitrogen adsorption experiments is shown in FIG. 4B, indicating a narrow distribution in the range of about 2.5 to 3.7 nm. FIGS. 5 and 6 show the development of body weight, body fat composition and lean in this study. FIGS. 5 and 6 are equivalent to FIGS. 2 and 3 as described in Example 2A, respectively.

No differences in body fat composition or body weight are observed in the female obese mice receiving silica particles in the diet compared to the control (FIG. 5).

Both body fat composition and body weight show a tendency to decrease in the group receiving porous silica in the diet compared to the control group not receiving porous silica in the experiment utilizing male mice (FIG. 6).

A mesoporous material with pore sizes in the order above 3 nm was utilized to exemplify the positive weight and cholesterol lowering properties of a porous silica. The effect of silica mesoporous particles with large pores, above 10 nm intake on blood lipid levels in obese black 6 mice (C57BL/6J) with elevated lipid/cholesterol blood levels and healthy animals is analyzed. Particles are embedded in the food pellets and given to the animals during a period of time of about 12 weeks. Blood levels of cholesterol, high-density lipoprotein cholesterol, low-density lipoprotein cholesterol and triglycerides are analyzed during the 12 weeks of particle intake. Levels of silica in blood are measured at the end of the experiment. Example 2C: A larger pore mesoporous silica material (Particle 3 which is representative for Silica 5 described in Table 2) Another study was performed as described in Example 2A, but utilizing a mesoporous silica material with a pore width of about 25 nm (Particle 3) instead of the material named Particle 2. FIG. 7A shows the SEM image of the material utilized in this study, Particle 3. The material's pore size distribution measured by nitrogen adsorption is shown in FIG. 7B indicating the distribution to be in the range of about 10 to 35 nm.

Both body fat composition and body weight show a tendency to decrease in the group receiving porous silica in the diet compared to the control group not receiving porous silica (FIG. 8).

Example 3: Food Intake and Adsorbed Silica for Particle 1 and Particle 2

The food intake of mice included in Example 2A and 2B was measured. The daily food intake is the same for mice receiving particles in the diet as in the control animals not receiving silica particles in the diet (FIGS. 9 A and C for Particle 1 and Particle 2 respectively).

The silica concentration in blood was measured by inductively coupled plasma technique at the end of the studies (after about 12 weeks of silica particle administration in the diet). No differences in blood silica content are observed between mice receiving porous silica in the diet and control mice not receiving porous silica in the diet after about 12 weeks of oral administration (FIGS. 9 B and D for Particle 1 and Particle 2 respectively).

Example 4: Cholesterol, HDL, P Glucose and Triglyceride Levels in Blood for Particle 1, Particle 2 and Particle 3

The Cholesterol, HDL, Glucose and Triglyceride levels in blood were analyzed at the end of the studies described in examples 2A, 2B and 2C.

No differences in blood lipid or glucose levels are observed between female mice receiving Particle 2 or Particle 1 in the diet, compared to control mice not receiving mesoporous silica in the diet after about 12 weeks of oral administration (respectively FIG. 10 and FIG. 11). Similar results are obtained for male mice, where no differences in blood lipid levels are observed between mice receiving Particle 1, Particle 2 or Particle 3 in the diet, compared to the control mice not receiving mesoporous silica in the diet after about 12 weeks of oral administration (FIG. 12).

Example 5: Example of a Bimodal Pore Mesoporous Material with Macropores (which is Representative for Silica 5 Described in Table 2)

Figure 1:
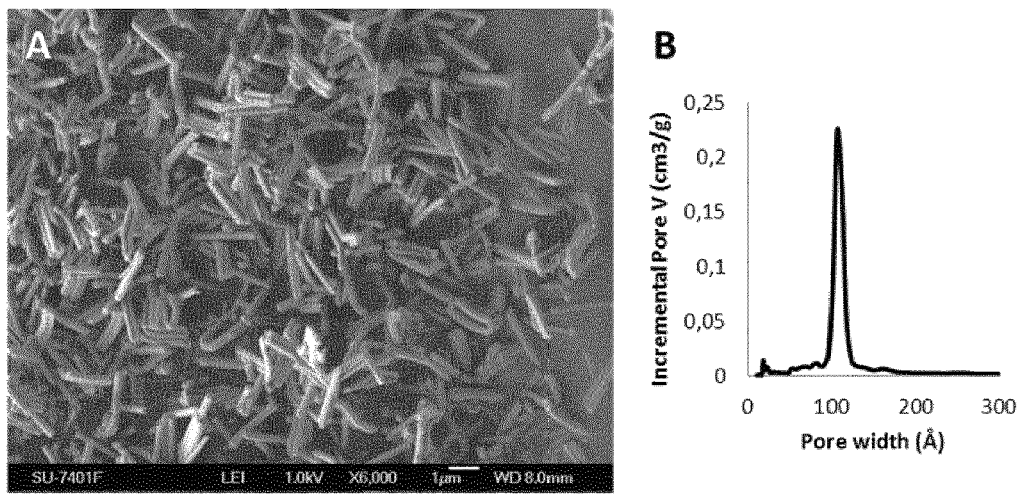
Figure 2:
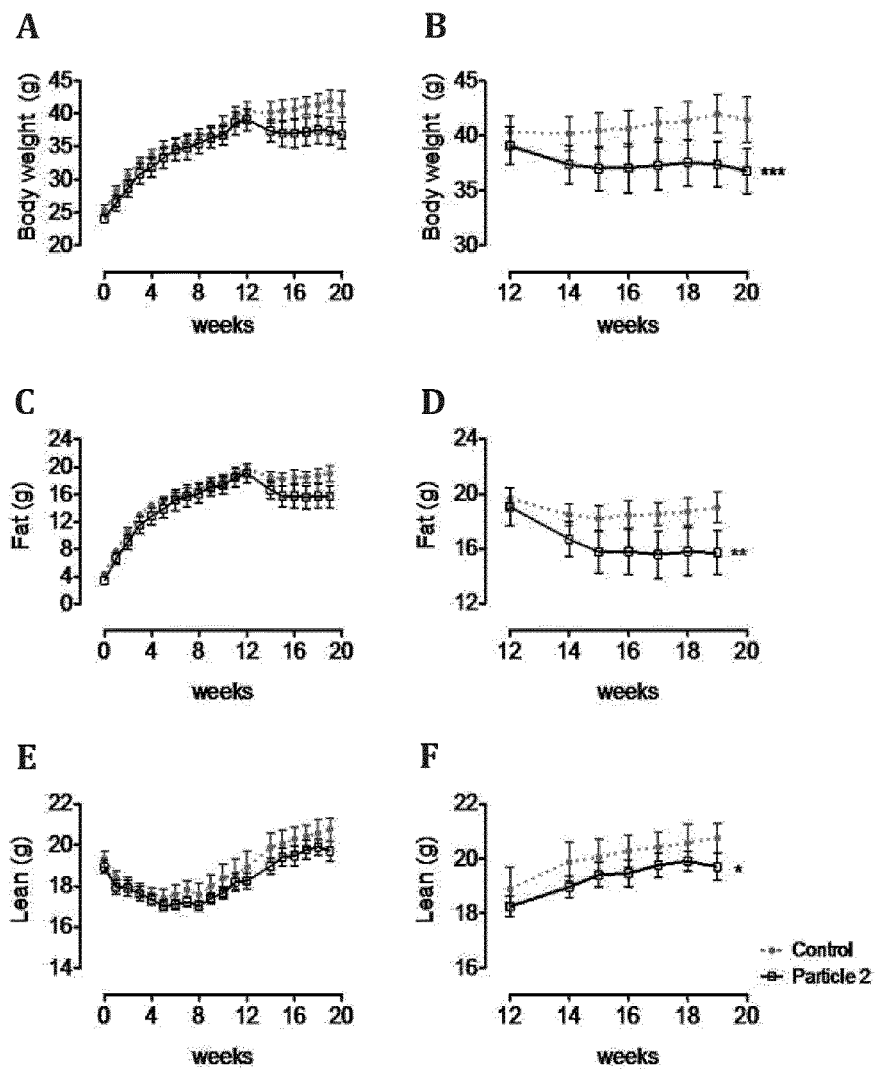
Figure 3:
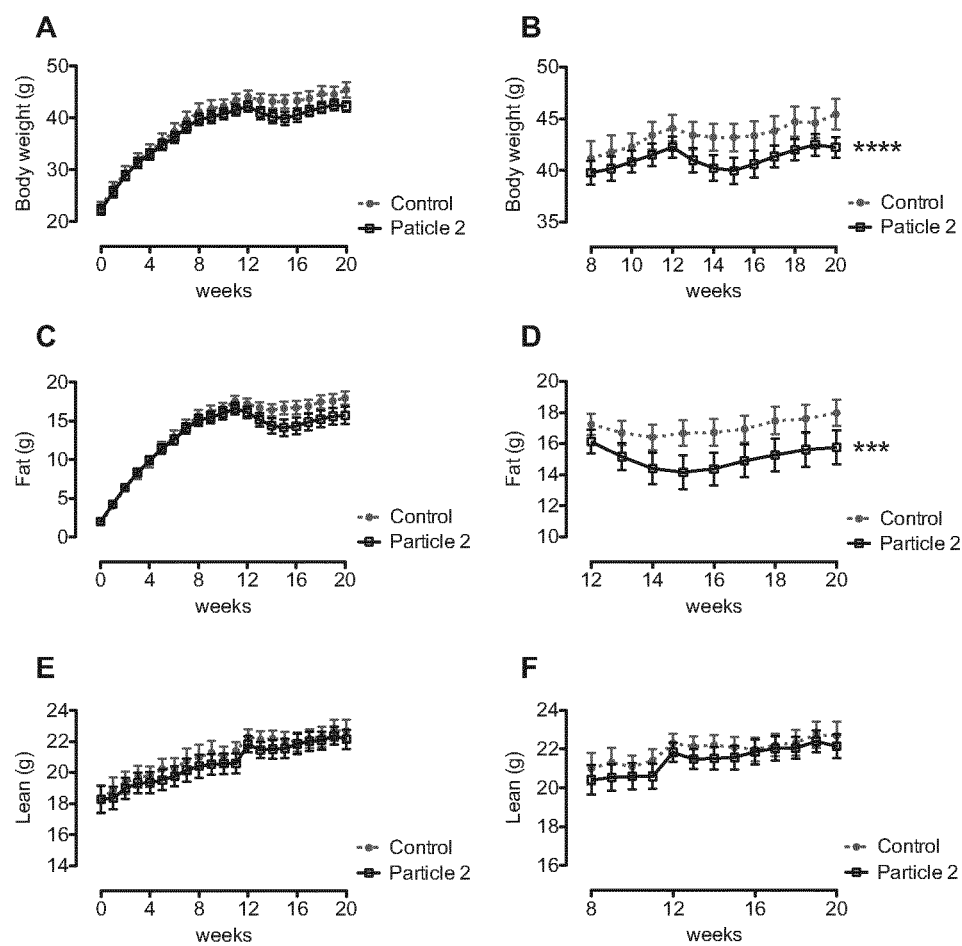
Figure 4:
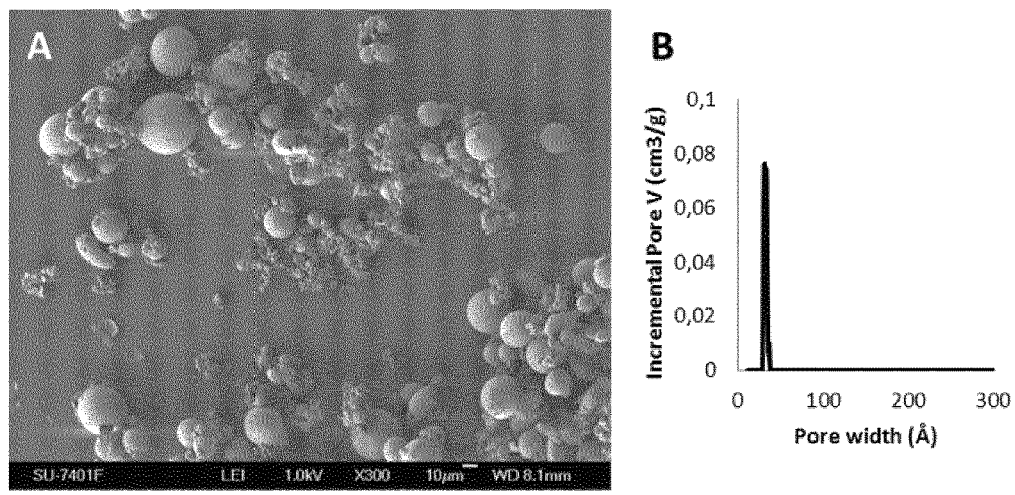
Figure 5:
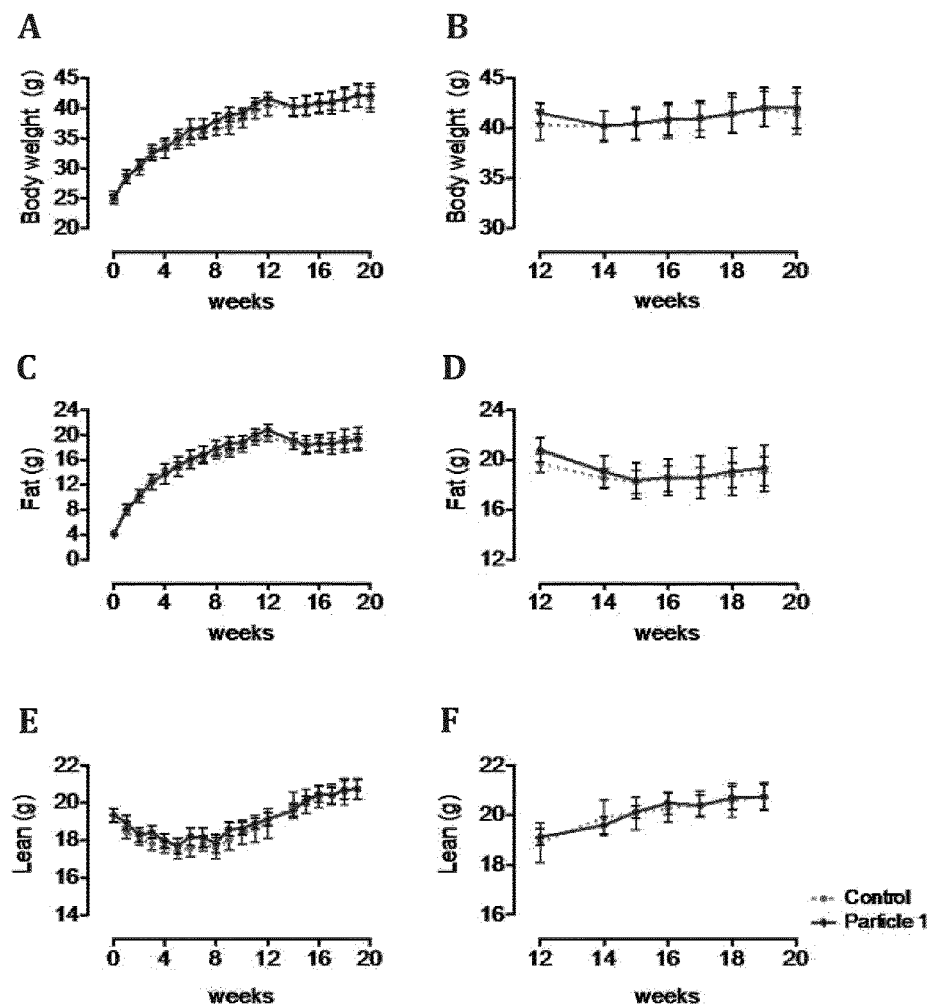
Figure 6:
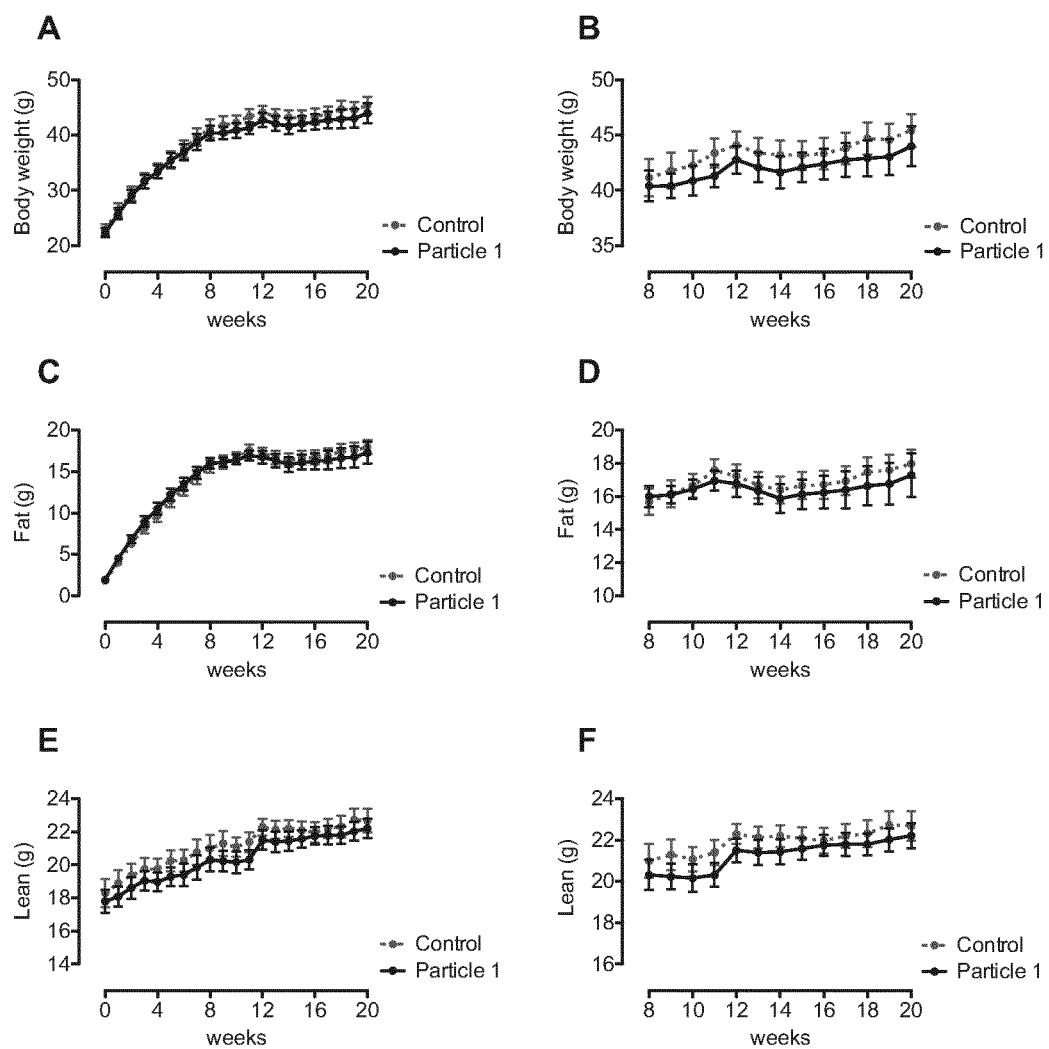
Figure 7:
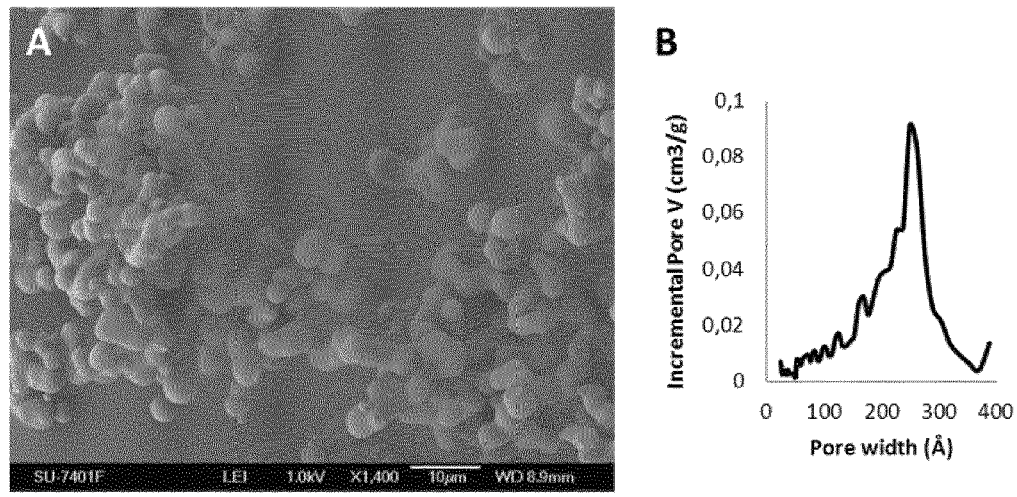
Figure 8:
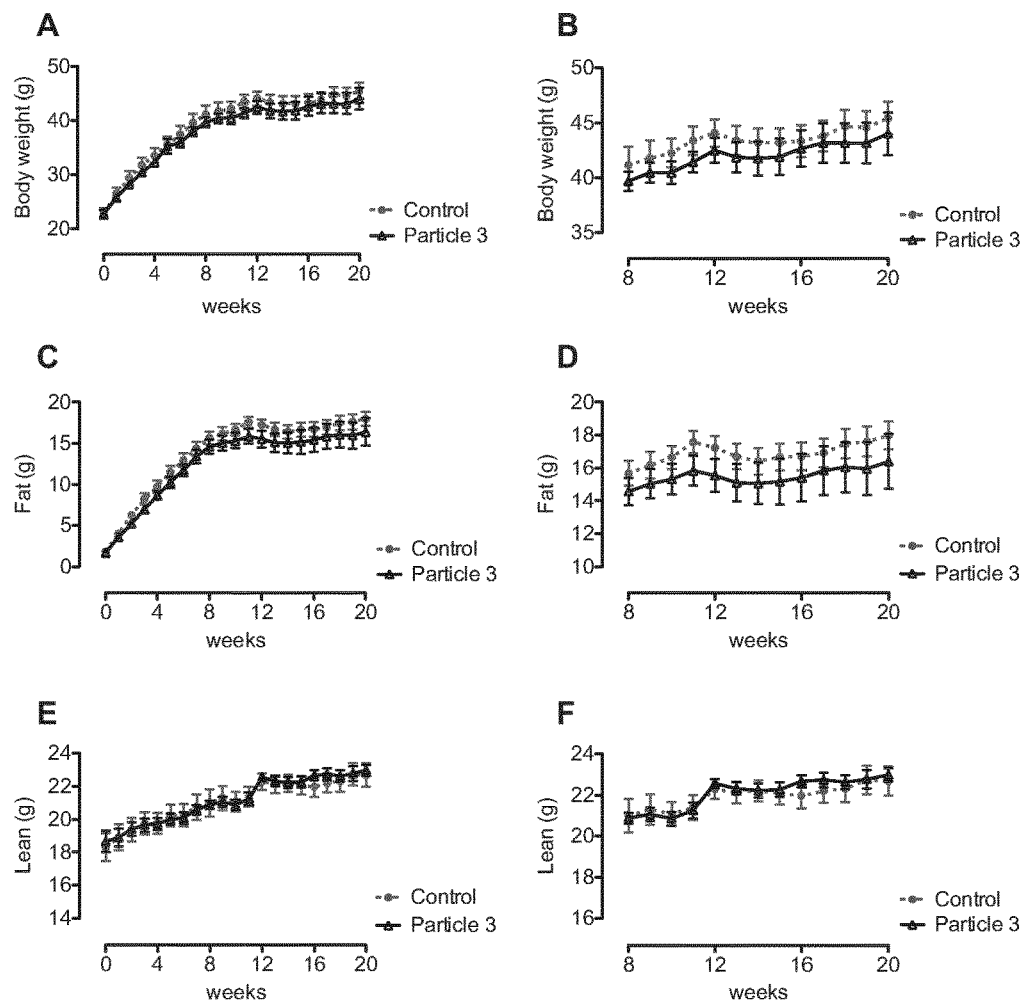
Figure 9:
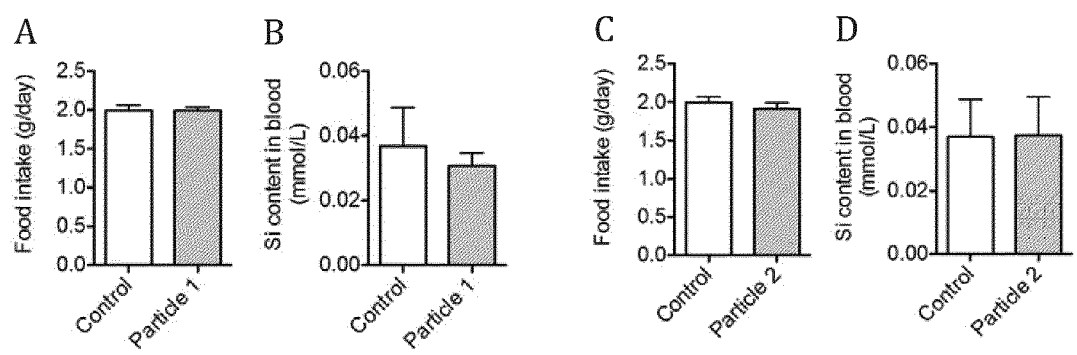
Figure 10:
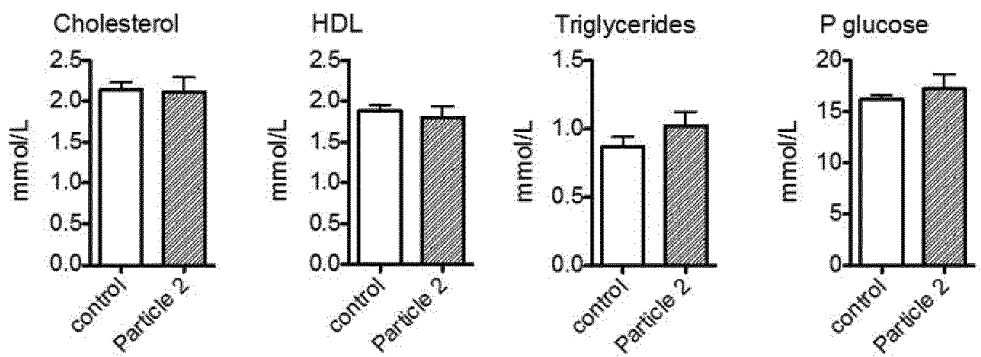
Figure 11:
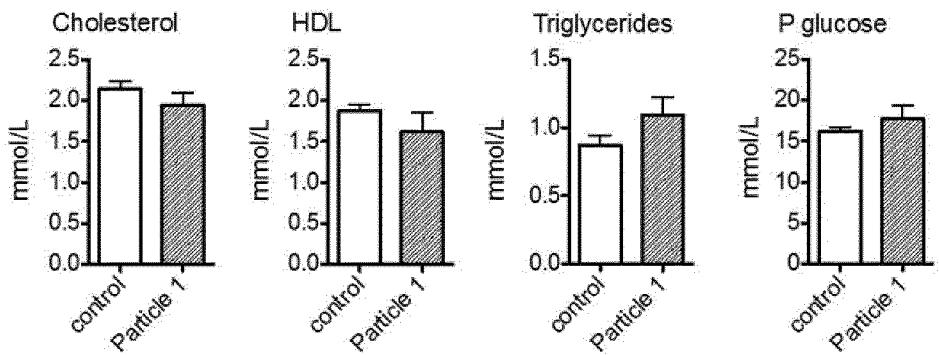
Figure 12:
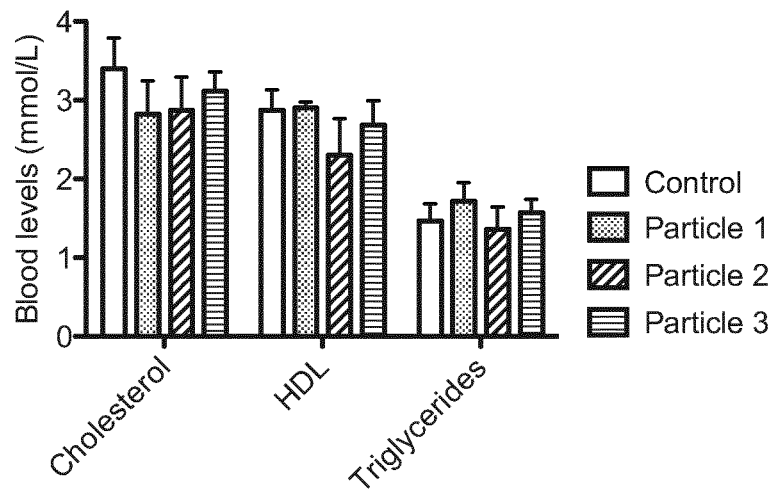
Figure 13:
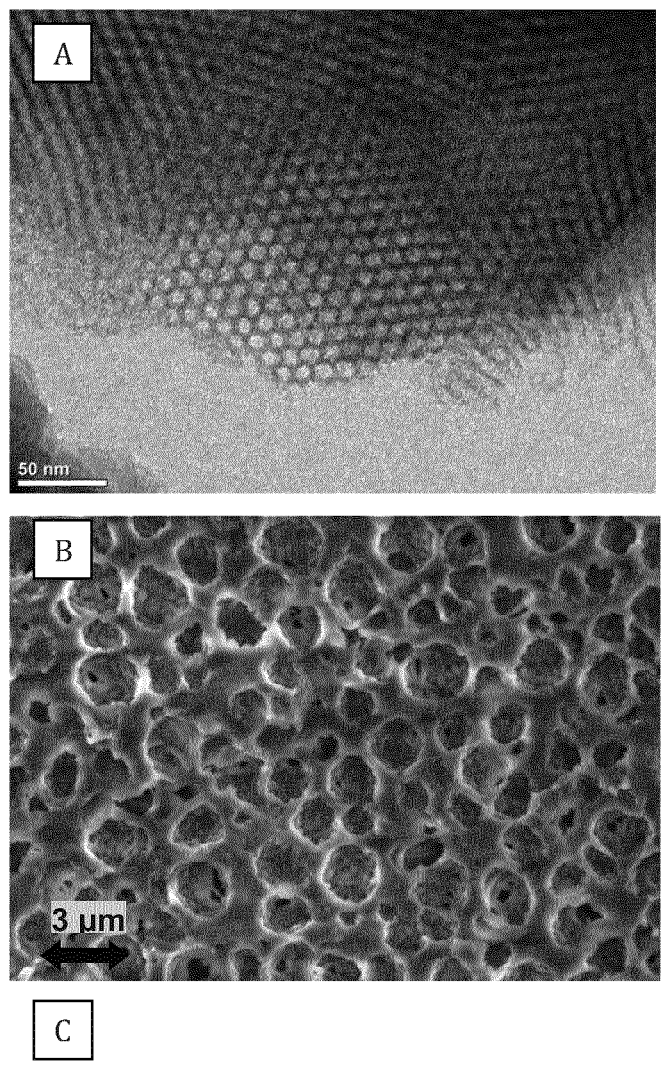
FIG. 13A shows an SEM image of a material representative for Silica 5 as described in Table 2.
FIG. 13B shows a transmission electron microscopy (TEM) image of the same material. A more detailed description of the material is summarized in the table in FIG. 13 C.

The invention claimed is:

1. A method of reduction in the risk of developing or treatment of: metabolic syndrome, type 2 diabetes, insulin resistance, or hyperglycemia in a human or animal in need thereof, comprising orally administering to the human or animal an effective amount of a porous silica material having pores in the mesoscale range of 2-50 nm, wherein the average pore size of the pores in the mesoscale range is in the range of 2 to 25 nm, and the pore size distribution (PSD) in the mesoscale range is such that at least 80% of the pores fall within the range of 2 to 25 nm; and wherein the porous silica material is precipitated silicon dioxide and the porous silica material excludes zeolites, and wherein the porous silica material has a minimum particle size distribution of 300 nm, and wherein the porous silica material is not systemically adsorbed, and wherein the porous silica material is the sole active ingredient being administered to the human or animal for reduction in the risk of developing or treatment of: metabolic syndrome, type 2 diabetes, insulin resistance or hyperglycemia.

2. A method of lowering glucose levels in the blood in a human or animal in need thereof, comprising orally administering to the human or animal an effective amount of a porous silica material having pores in the mesoscale range of 2-50 nm, wherein the average pore size of the pores in the mesoscale range is in the range of 2 to 25 nm, and the pore size distribution (PSD) in the mesoscale range is such that at least 80% of the pores fall within the range of 2 to 25 nm; and wherein the porous silica material is precipitated silicon dioxide and the porous silica material excludes zeolites, and wherein the porous silica material has a minimum particle size distribution of 300 nm, and wherein the porous silica material is not systemically adsorbed, and wherein the porous silica material is the sole active ingredient being administered to the human or animal for lowering glucose levels in the blood.

3. The method of claim 1, wherein reduction in the risk of developing or treatment of: metabolic syndrome, type 2 diabetes, insulin resistance, or hyperglycemia in a human or animal is achieved by reduction of adipose tissue in the human or animal.

4. The method of claim 1, wherein the human or animal is obese.

5. The method of claim 1, wherein the average pore size is in the range of 7 to 15 nm.

6. The method of claim 1, wherein the average pore size is in the range of 10 to 12 nm.

7. The method of claim 1, wherein the BET (Brunauer-Emmett-Teller theory) surface area is between 300 and 1300 m$^2$/g.

8. The method of claim 7, wherein the BET surface area is between 500 and 900 m$^2$/g.

9. The method of claim 1, wherein the pore volume measured by nitrogen adsorption is in the range of 0.3 to 1.7 cm$^3$/g.

10. The method of claim 1, wherein the porous silica material additionally has a hierarchical porous structure containing both pores in the range of 2 to 50 nm and pores larger than 50 nm.

11. The method of claim 2, wherein the lowering glucose levels in the blood in a human or animal is achieved by reduction of adipose tissue in the human or animal.

12. The method of claim 2, wherein the human or animal is obese.

13. The method of claim 2, wherein the average pore size is in the range of 7 to 15 nm.

14. The method of claim 2, wherein the average pore size is in the range of 10 to 12 nm.

15. The method of claim 2, wherein the BET (Brunauer-Emmett-Teller theory) surface area is between 300 and 1300 m$^2$/g.

16. The method of claim 15, wherein the BET surface area is between 500 and 900 m$^2$/g.

17. The method of claim 2, wherein the pore volume measured by nitrogen adsorption is in the range of 0.3 to 1.7 cm$^3$/g.

18. The method of claim 2, wherein the porous silica material additionally has a hierarchical porous structure containing both pores in the range of 2 to 50 nm and pores larger than 50 nm.

19. The method of claim 1, wherein the method is a method of reduction in the risk of developing: metabolic syndrome or type 2 diabetes in a human at risk of developing metabolic syndrome or type 2 diabetes.

* * * * *